US008749625B2

(12) United States Patent
Hashimoto

(10) Patent No.: US 8,749,625 B2
(45) Date of Patent: Jun. 10, 2014

(54) METHOD FOR RESETTING CMOS IMAGING ELEMENT IN ENDOSCOPE APPARATUS

(75) Inventor: Kunio Hashimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 614 days.

(21) Appl. No.: 13/016,617

(22) Filed: Jan. 28, 2011

(65) Prior Publication Data

US 2011/0242300 A1    Oct. 6, 2011

(30) Foreign Application Priority Data

Mar. 30, 2010    (JP) ................................. 2010-078147

(51) Int. Cl.
*A61B 1/00*    (2006.01)
(52) U.S. Cl.
CPC ................................. *A61B 1/00006* (2013.01)
USPC .......................................................... 348/65
(58) Field of Classification Search
USPC ........ 348/311, 308, 65, 72, 74; 600/109, 110, 600/118
See application file for complete search history.

(56) References Cited

U.S. PATENT DOCUMENTS

| 3,716,704 | A | * | 2/1973 | Dixon | 377/2 |
| 5,140,177 | A | * | 8/1992 | Suda et al. | 326/21 |
| 6,638,212 | B1 | * | 10/2003 | Oshima | 600/109 |
| 7,593,051 | B2 | * | 9/2009 | Suda | 348/311 |
| 2009/0213212 | A1 | * | 8/2009 | Nakamura | 348/65 |

FOREIGN PATENT DOCUMENTS

| EP | 2 096 865 A2 | 9/2009 |
| JP | 2009077846 A * | 4/2009 |
| JP | 2009-201540 A | 9/2009 |

OTHER PUBLICATIONS

A low-cost solution for developing reliable Linuxbased space computers for on-board data handling, 2009 15th IEEE International On-Line Testing Symposium (IOLTS 2009), pp. 49-54.*

* cited by examiner

*Primary Examiner* — Tung Vo
*Assistant Examiner* — Joseph Becker
(74) *Attorney, Agent, or Firm* — Sughrue Mion, PLLC

(57) ABSTRACT

According to an aspect of the present invention, when the CMOS imaging element is out of control, the soft reset and the device reset which partially initialize the CMOS imaging element are sequentially performed before the CMOS imaging element is reset by stopping the power supply where it takes long before the CMOS imaging element is restored. Thus, when the CMOS imaging element is restored to a normal state by one of the reset steps, the time to restore the CMOS imaging element can be substantially reduced.

19 Claims, 6 Drawing Sheets

METHOD FOR RESETTING CMOS IMAGING ELEMENT IN ENDOSCOPE APPARATUS

BACKGROUND OF THE INVENTION

1. Field of the Invention

The present invention relates to a method for resetting a CMOS imaging element in an endoscope apparatus, and more particularly, to a method for resetting a CMOS imaging element in an endoscope apparatus where a CMOS imaging element which takes an endoscope image is used at the distal end of an endoscope insertion portion.

2. Description of the Related Art

Examination using an endoscope apparatus, for example, an electronic endoscope has been quite popular in the medical field. In the electronic endoscope, an image sensor such as a CCD sensor and a CMOS sensor is mounted at the distal end of an insertion portion to be inserted into a subject, and is connected to a processor apparatus (a signal processing apparatus) through a cord or a connector. The processor apparatus performs various processing on an imaging signal obtained from the image sensor, and generates an endoscope image for use in diagnosis. The endoscope image is displayed on a monitor connected to the processor apparatus.

CCD sensors have been generally used as the image sensor provided at the endoscope insertion portion. However, the use of CMOS sensors has been considered recently (for example, see Japanese Patent Application Laid-Open No. 2009-201540). The CMOS sensors are different from the CCD sensors, and can be formed as a CMOS imaging element by a general CMOS manufacturing process on the same chip as peripheral circuits such as a signal processing circuit, a timing generator, an A/D converter, and a communication interface.

SUMMARY OF THE INVENTION

In an endoscope apparatus using a CCD sensor, peripheral circuits of the CCD sensor are arranged on a relay board of an operation portion apart from the CCD sensor provided at the distal end of an endoscope insertion portion, and a processor apparatus transmits and receives signals to and from the relay board. An imaging signal from the CCD sensor is transmitted as an analog signal to the relay board. Meanwhile, in an endoscope using the CMOS imaging element as described above, an imaging signal converted into a digital signal is directly transmitted between the CMOS imaging element at the distal end of an endoscope insertion portion and a processor apparatus or a relay board, and a control signal is directly transmitted and received therebetween through serial communication.

Thus, the quality of a communication channel for the imaging signal or the control signal, the malfunction of the CMOS imaging element and the like become a problem in the endoscope using the CMOS imaging element. Particularly, the distal end of the endoscope insertion portion is easily affected by electrical noise when observation is performed together with APC (Argon Plasma Coagulation), or when an electrical treatment instrument is used. The CMOS imaging element may be thereby out of control, so that an endoscope image cannot be obtained.

To avoid such a state, power supply to the CMOS imaging element may be temporarily turned OFF to restore the CMOS imaging element to an initial state. However, once the CMOS imaging element is turned OFF, it takes too long before the CMOS imaging element is operational after being turned ON. Thus, it is preferable that the CMOS imaging element can be restored as quickly as possible.

The present invention has been made in view of such circumstances, and it is an object of the invention to provide a method for resetting a CMOS imaging element in an endoscope apparatus where a CMOS imaging element which takes an endoscope image is provided at the distal end of an endoscope insertion portion, the method capable of restoring the CMOS imaging element to a normal state as quickly as possible when the CMOS imaging element is out of control.

In order to achieve the above object, a method for resetting a CMOS imaging element in an endoscope apparatus according to a first aspect of the present invention is a method for resetting a CMOS imaging element in an endoscope apparatus where a CMOS imaging element which takes an endoscope image is provided at a distal end of an insertion portion, the method restoring the CMOS imaging element to a normal state when the CMOS imaging element is out of control, including: a first reset step of executing soft reset to initialize a register of the CMOS imaging element; a second reset step of executing device reset to initialize a signal processing section of the CMOS imaging element when the CMOS imaging element is not restored to a normal state by the first reset step; and a third reset step of temporarily stopping power supply to the CMOS imaging element and restarting the power supply when the CMOS imaging element is not restored to a normal state by the second reset step.

According to the first aspect, when the CMOS imaging element is out of control, the soft reset and the device reset which partially initialize the CMOS imaging element are sequentially performed before the CMOS imaging element is reset by stopping the power supply where it takes long before the CMOS imaging element is restored. Thus, when the CMOS imaging element is restored to a normal state by one of the reset steps, the time to restore the CMOS imaging element can be substantially reduced.

The method for resetting a CMOS imaging element in an endoscope apparatus according to a second aspect of the present invention is the invention according to the first aspect, wherein the endoscope apparatus is connected to a processor apparatus which processes an imaging signal output from the CMOS imaging element and displays an endoscope image on a monitor, and the first reset step is executed by a control signal given from the processor apparatus or a control circuit in the endoscope apparatus to a serial communication terminal of the CMOS imaging element.

According to the second aspect, the soft reset in the first reset step is performed by initializing the register based on the control signal given from the processor apparatus or the control circuit in the endoscope apparatus through serial communication.

The method for resetting a CMOS imaging element in an endoscope apparatus according to a third aspect of the present invention is the invention according to the first or second aspect, wherein the endoscope apparatus is connected to a processor apparatus which processes an imaging signal output from the CMOS imaging element and displays an endoscope image on a monitor, and the second reset step is executed by a reset signal given from the processor apparatus or a control circuit in the endoscope apparatus to a device reset terminal of the CMOS imaging element.

According to the third aspect, the device reset in the second reset step is performed by giving a predetermined reset signal to the device reset terminal of the CMOS imaging element from the processor apparatus or the control circuit in the endoscope apparatus.

The method for resetting a CMOS imaging element in an endoscope apparatus according to a fourth aspect of the present invention is the invention according to the first, second or third aspect, wherein the endoscope apparatus is connected to a processor apparatus which processes an imaging signal output from the CMOS imaging element and displays an endoscope image on a monitor, and the third reset step is executed by temporarily stopping power supply from the processor apparatus or a control circuit in the endoscope apparatus to a power terminal of the CMOS imaging element.

According to the fourth aspect, the power supply stop and restart in the third reset step is performed by temporarily stopping the power supply to the power terminal of the CMOS imaging element from the processor apparatus or the control circuit in the endoscope apparatus.

The method for resetting a CMOS imaging element in an endoscope apparatus according to a fifth aspect of the present invention is the invention according to the first, second, third or fourth aspect, wherein the endoscope apparatus is connected to a processor apparatus which processes an imaging signal output from the CMOS imaging element and displays an endoscope image on a monitor, and whether or not the CMOS imaging element is in a normal state is determined based on whether or not there is a response from the CMOS imaging element to a control signal transmitted from the processor apparatus or a control circuit in the endoscope apparatus to a serial communication terminal of the CMOS imaging element.

According to the fifth aspect, whether or not the CMOS imaging element is in a normal state, that is, whether or not the CMOS imaging element is out of control is determined based on the serial communication between the CMOS imaging element and the processor apparatus or the control circuit in the endoscope apparatus.

The method for resetting a CMOS imaging element in an endoscope apparatus according to a sixth aspect of the present invention is the invention according to the first, second, third or fourth aspect, wherein the endoscope apparatus is connected to a processor apparatus which processes an imaging signal output from the CMOS imaging element and displays an endoscope image on a monitor, and whether or not the CMOS imaging element is in a normal state is determined by including additional information indicating an operation state of the CMOS imaging element in the imaging signal in the CMOS imaging element and reading out the additional information by the processor apparatus.

According to the sixth aspect, whether or not the CMOS imaging element is in a normal state, that is, whether or not the CMOS imaging element is out of control is determined based on the additional information contained in the imaging signal output from the CMOS imaging element to the processor apparatus.

The method for resetting a CMOS imaging element in an endoscope apparatus according to a seventh aspect of the present invention is the invention according to the first, second, third or fourth aspect, wherein the endoscope apparatus is connected to a processor apparatus which processes an imaging signal output from the CMOS imaging element and displays an endoscope image on a monitor, and whether or not the CMOS imaging element is in a normal state is determined in the processor apparatus, based on a change in the endoscope image by the imaging signal.

According to the seventh aspect, whether or not the CMOS imaging element is in a normal state, that is, whether or not the CMOS imaging element is out of control is determined based on the change in the endoscope image by the imaging signal output from the CMOS imaging element to the processor apparatus.

The method for resetting a CMOS imaging element in an endoscope apparatus according to an eighth aspect of the present invention is the invention according to any one of the first to seventh aspects, wherein the device reset in the second reset step can be disabled.

According to the eighth aspect, a failure that the device reset is unintentionally executed due to electrical noise or the like can be prevented.

In the present invention, when the CMOS imaging element is out of control in the endoscope apparatus where the CMOS imaging element which takes the endoscope image is provided at the distal end of the endoscope insertion portion, the CMOS imaging element can be restored to a normal state as quickly as possible.

DETAILED DESCRIPTION OF THE PREFERRED EMBODIMENTS

In the following, a preferred embodiment of a method for resetting a CMOS imaging element in an endoscope according to the present invention will be described in detail by reference to the accompanying drawings.

Figure 1:
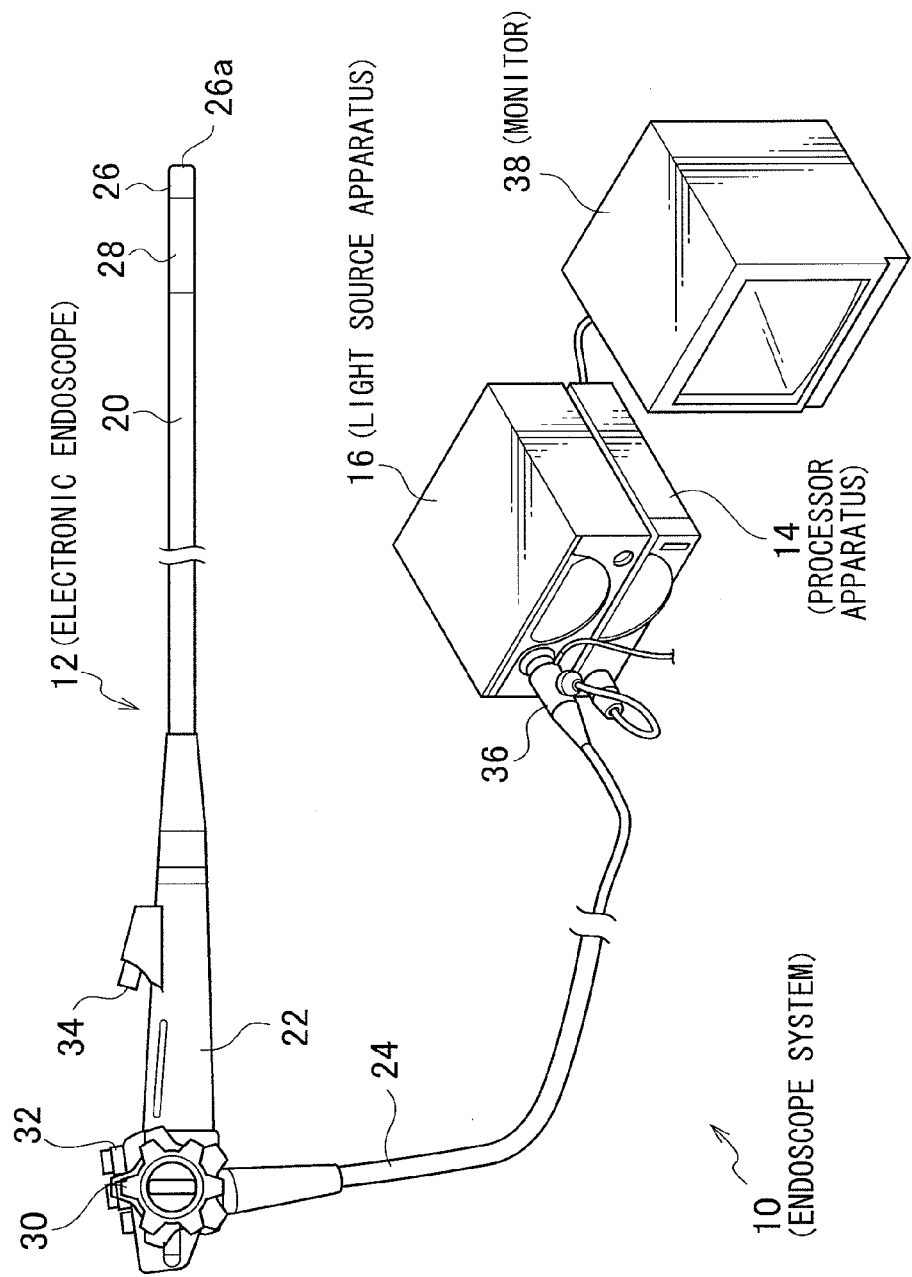
FIG. 1 is an entire configuration diagram illustrating the schematic configuration of an endoscope system.

FIG. 1 is an entire configuration diagram illustrating the schematic configuration of an endoscope system according to one embodiment of the present invention. As shown in FIG. 1, an endoscope system 10 according to the present embodiment includes an endoscope apparatus (an electronic endoscope, referred to as endoscope below) 12, a processor apparatus 14, and a light source apparatus 16. The endoscope 12 includes a flexible insertion portion 20 to be inserted into a body cavity of a patient (a subject), an operation portion 22 provided continuously to a proximal end portion of the insertion portion 20, and a universal cord 24 connected to the processor apparatus 14 and the light source apparatus 16.

A distal end portion 26 where a CMOS imaging element (an imaging chip) 54 which takes an image of the inside of a body cavity (see FIG. 3) or the like is incorporated is provided continuously to the distal end of the insertion portion 20. A bending portion 28 where a plurality of bending pieces are connected together is provided posterior to the distal end portion 26. The bending portion 28 bends vertically and horizontally when an angle knob 30 provided on the operation portion 22 is operated to push and pull a wire inserted through the insertion portion 20. The distal end portion 26 is thereby oriented in a desired direction in a body cavity.

The proximal end of the universal cord 24 is connected to a connector 36. The connector 36 is of composite type. The processor apparatus 14 is connected to the connector 36, and the light source apparatus 16 is also connected thereto.

The processor apparatus 14 feeds power to the electronic endoscope 12 through a cable 68 (see FIG. 3) inserted through the universal cord 24 to control the driving of the CMOS imaging element 54. The processor apparatus 14 also receives an imaging signal transmitted from the CMOS imaging element 54 through the cable 68 and performs various signal processing on the received imaging signal to convert the signal into image data. The image data converted in the processor apparatus 14 is displayed as an endoscope image on a monitor 38 connected to the processor apparatus 14 through a cable. The processor apparatus 14 is also electrically connected to the light source apparatus 16 through the connector 36 to collectively control the operation of the endoscope system 10.

Figure 2:
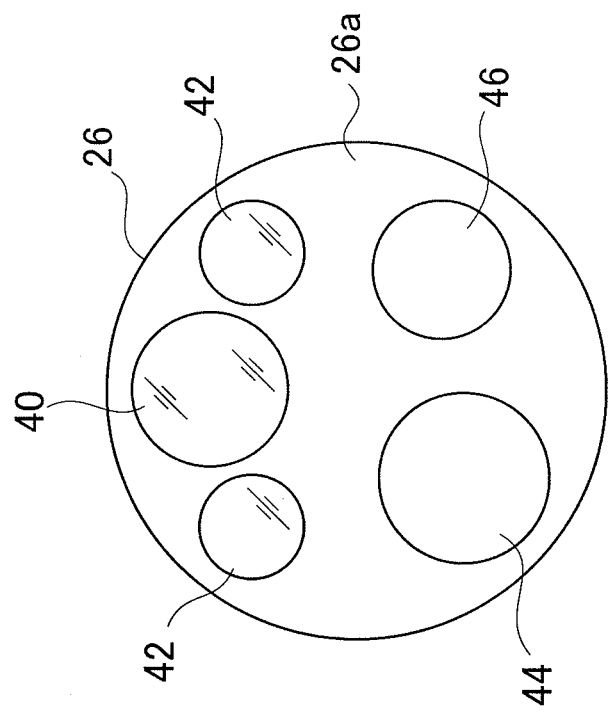
FIG. 2 is a front view illustrating a distal end portion of an electronic endoscope.

FIG. 2 is a front view illustrating the distal end portion 26 of the electronic endoscope 12. As shown in FIG. 2, an observation window 40, illumination windows 42, a forceps outlet 44, and an air/water supply nozzle 46 are provided in a distal end surface 26a of the distal end portion 26. The observation window 40 is arranged in the center on one side of the distal end portion 26. The illumination windows 42 are arranged at two positions symmetrical with respect to the observation window 40 to project illumination light from the light source apparatus 16 onto a region to be observed in a body cavity. The forceps outlet 44 is connected to a forceps channel 70 (see FIG. 3) provided in the insertion portion 20 to communicate with a forceps inlet 34 (see FIG. 1) provided in the operation portion 22. Various treatment instruments where an injection needle, a diathermy knife or the like is provided at the distal end are inserted into the forceps inlet 34, and the distal ends of various treatment instruments are exposed from the forceps outlet 44. The air/water supply nozzle 46 sprays cleaning water or air supplied from an air/water supply device incorporated in the light source apparatus 16 to the observation window 40 or into a body cavity according to the operation of an air/water supply button 32 (see FIG. 1) provided on the operation portion 22.

Figure 3:
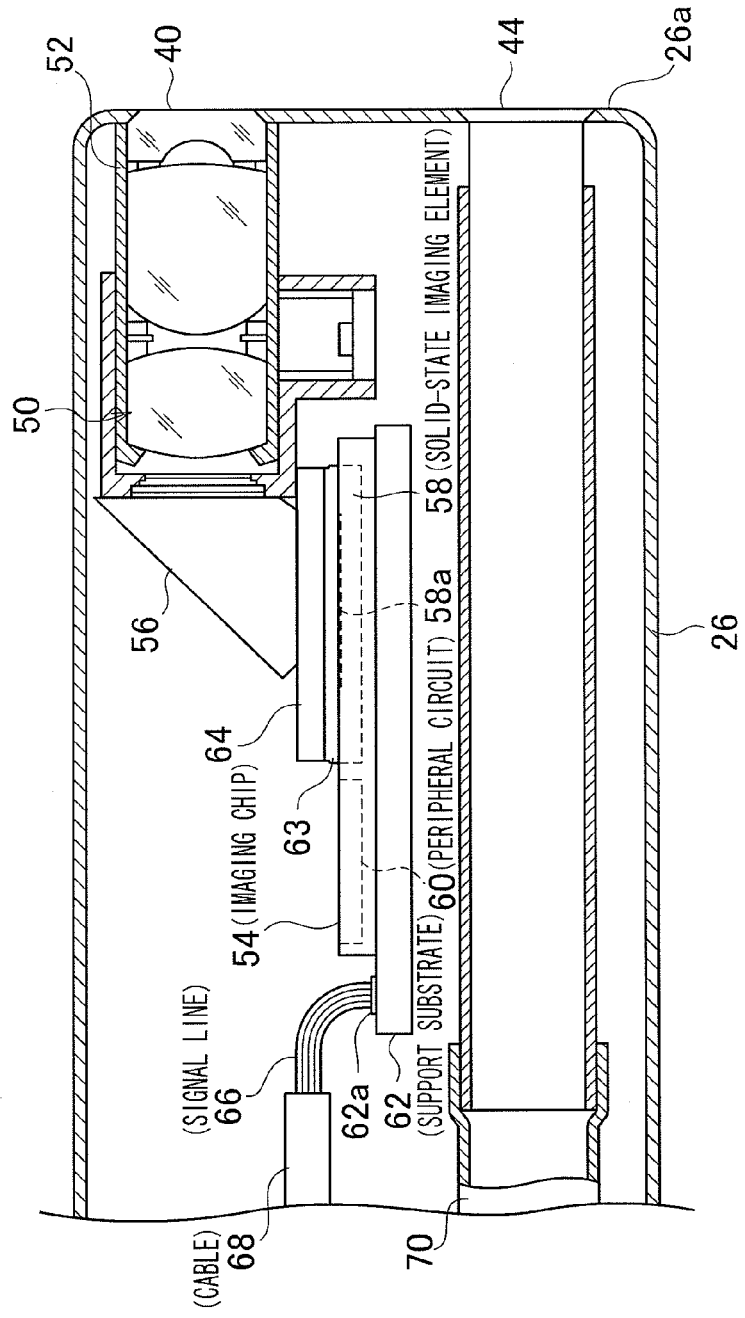
FIG. 3 is a side sectional view illustrating the distal end portion of the electronic endoscope.

FIG. 3 is a side sectional view illustrating the distal end portion 26 of the endoscope 12. As shown in FIG. 3, a lens barrel 52 which holds an objective optical system 50 for receiving image light of an observed region in a body cavity is provided posterior to the observation window 40. The lens barrel 52 is mounted such that the optical axis of the objective optical system 50 is parallel to the center axis of the insertion portion 20. A prism 56 which guides the image light of the observed region from the objective optical system 50 toward the imaging chip 54 by bending the image light at a substantially right angle is connected to the rear end of the lens barrel 52.

The CMOS imaging element 54 is a monolithic semiconductor (a so-called CMOS sensor chip) where a CMOS sensor 58 and peripheral circuits which drive the CMOS sensor 58 and input and output a signal into and from the CMOS sensor 58 are integrally formed, and is mounted on a support substrate 62. An imaging surface 58a of the CMOS sensor 58 is arranged facing an emission surface of the prism 56. A cover glass 64 having a rectangular plate shape is attached onto the imaging surface 58a via a spacer 63 having a rectangular frame shape. The CMOS sensor 58, the spacer 63, and the cover glass 64 are bonded together with an adhesive. The imaging surface 58a is thereby protected from ingress of dust or the like.

A plurality of input-output terminals 62a are provided side by side in the width direction of the support substrate 62 which is extended toward the rear end of the insertion portion 20 in a rear end portion of the support substrate 62. Signal lines 66 are bonded to the input-output terminals 62a to mediate an exchange of various signals between the input-output terminals 62a and the processor apparatus 14 through the universal cord 24. The input-output terminals 62a are electrically connected to the peripheral circuits 60 inside the CMOS imaging element 54 through a wire or a bonding pad (not shown) formed on the support substrate 62. The signal lines 66 are inserted in a bundle into the flexible tubular cable 68. The cable 68 is inserted through the inside of each of the insertion portion 20, the operation portion 22, and the universal cord 24, and connected to the connector 36.

Although not shown in the drawings, an illumination portion is provided posterior to the illumination window 42. An emission end of a light guide which guides the illumination light from the light source apparatus 16 is arranged at the illumination portion. The light guide is inserted through the inside of each of the insertion portion 20, the operation portion 22, and the universal cord 24, and its incident end is connected to the connector 36 in a similar manner to the cable 68.

Figure 4:
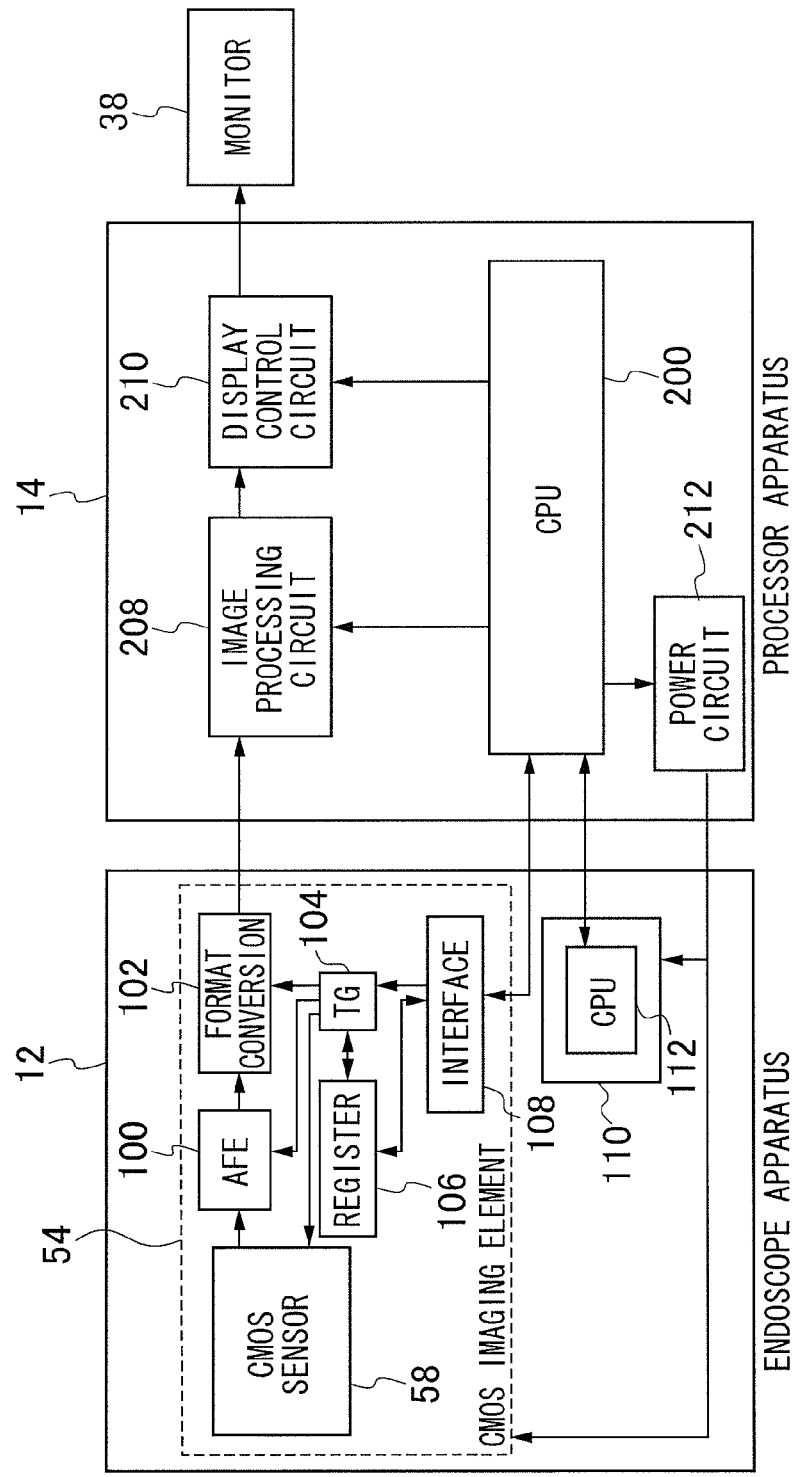
FIG. 4 is a block diagram illustrating the configuration of a control system of the endoscope system including an endoscope apparatus and a processor apparatus.

FIG. 4 is a block diagram illustrating the configuration of the endoscope 12 and the processor apparatus 14 in the above endoscope system 10.

As shown in FIG. 4, the CMOS imaging element 54 where the CMOS sensor 58 and the peripheral circuits are formed on the same chip is incorporated in the distal end portion 26 of the endoscope 12 (the insertion portion 20). The peripheral circuits include an analog front end (AFE) 100, a format conversion circuit 102, a register 106, a timing generator (TG) 104, and an interface circuit 108.

The CMOS sensor 58 includes a photodiode formed for each of pixels arranged in a matrix, a voltage conversion circuit which converts signal charges accumulated in the photodiode into a voltage signal, a scanning circuit (a vertical scanning circuit and a horizontal scanning circuit) which specifies the address (the position) of a pixel whose voltage signal is to be read out from the voltage conversion circuit, and an output circuit which sequentially outputs the voltage signals of the pixels read out by the scanning circuit.

The AFE 100 includes a correlated double sampling circuit (CDS), an automatic gain control circuit (AGC), and an analog/digital converter (A/D). The CDS performs correlated double sampling processing on an imaging signal including the pixel signals sequentially read out from the pixels of the CMOS sensor 58, and eliminates reset noise and amplifier noise generated in the CMOS sensor 58. The AGC amplifies the imaging signal from which noise has been eliminated by the CDS at a gain (an amplification factor) specified by the processor apparatus 14. The A/D converts the imaging signal amplified by the AGC into a digital signal having a predetermined number of bits and outputs the digital signal. The format conversion circuit 102 converts the imaging signal digitalized and output by the A/D (the digital imaging signal) into a signal of a predetermined format determined in relation to the processor apparatus 14, and the signal is thereby transmitted to the processor apparatus 14.

The timing generator (TG) 104 generates a drive pulse for reading out the pixel signal from the CMOS sensor 58, and a synchronizing pulse for each section such as the AFE 100.

The register 106 is a memory which stores a parameter that determines the processing content of each section in the CMOS imaging element 54, and each section is processed according to the parameter.

The interface circuit 108 inputs a control signal (a command) which sets the processing content of each section of the CMOS imaging element 54, a basic clock or the like from outside the CMOS imaging element 54, and outputs information of the parameter or the like set in the register 106 to outside. When a command is input to the interface circuit 108, a parameter is set in the register 106 according to the command. The basic clock is given to the TG 104, and the pulse to be fed to each section is produced based thereon.

Although not always provided, a relay board 110 is mounted on the operation portion 22 of the endoscope 12. The relay board 110 includes a CPU 112 when a switch for electrical processing or the like is provided on the operation portion 22 or when zoom control or focus control of the objective optical system 50 (see FIG. 3) which forms an image of an object is performed on the CMOS sensor 58. The CPU 112 detects the state of the switch, and the objective optical system 50 is controlled by the CPU 112 and an unillustrated drive circuit. The CPU 112 is connected to a CPU 200 of the processor apparatus 14 via an unillustrated interface circuit. Information of the switch state relating to processing performed in the processor apparatus 14 is thereby transmitted to the CPU 200, and the CPU 200 executes the processing based on the switch state.

The processor apparatus 14 includes the CPU 200, an image processing circuit 208, and a display control circuit 210. The CPU 200 collectively controls the operation of each section in the processor apparatus 14, and also exchanges various signals with the endoscope 12 as described above. For example, the CPU 200 gives the control signal or the basic clock to the CMOS imaging element 54, and acquires the control information from the CMOS imaging element 54.

The image processing circuit 208 is shown in a simplified manner as a single circuit which performs image processing in the processor apparatus 14 such as color separation, color interpolation, gain correction, white balance adjustment, gamma correction, edge enhancement processing, and brightness adjustment processing on the input imaging signal. Image data obtained by giving the image processing on the imaging signal input into the image processing circuit 208 is input into the display control circuit 210 at the subsequent stage.

The display control circuit 210 generates a video signal according to the display format of the monitor 38 from the image data input from the image processing circuit 208, and outputs the video signal to the monitor 38. The monitor 38 thereby displays an endoscope image taken by the CMOS imaging element 54.

A power circuit 212 is a circuit which supplies power of a necessary voltage to each section of the processor apparatus 14, and the CMOS imaging element 54 and the relay board 110 of the endoscope 12.

The CPU 200 of the processor apparatus 14 may not be directly connected to the interface circuit 108 of the CMOS imaging element 54, but the CPU 112 of the relay board 110 in the endoscope 12 may be connected thereto. Accordingly, the exchange of signals between the CPU 200 of the processor apparatus 14 and the CMOS imaging element 54 may be performed via the CPU 112, or the CPU 112 may control the CMOS imaging element 54. Although reset control described below is entirely performed based on an instruction from the CPU 200 of the processor apparatus 14, the control may be also partly or entirely performed by the CPU 112 (a control circuit) in the endoscope 12, not the CPU 200.

A method for resetting the CMOS imaging element 54 in the endoscope 12 of the endoscope system 10 having the aforementioned configuration will be described.

Figure 5:
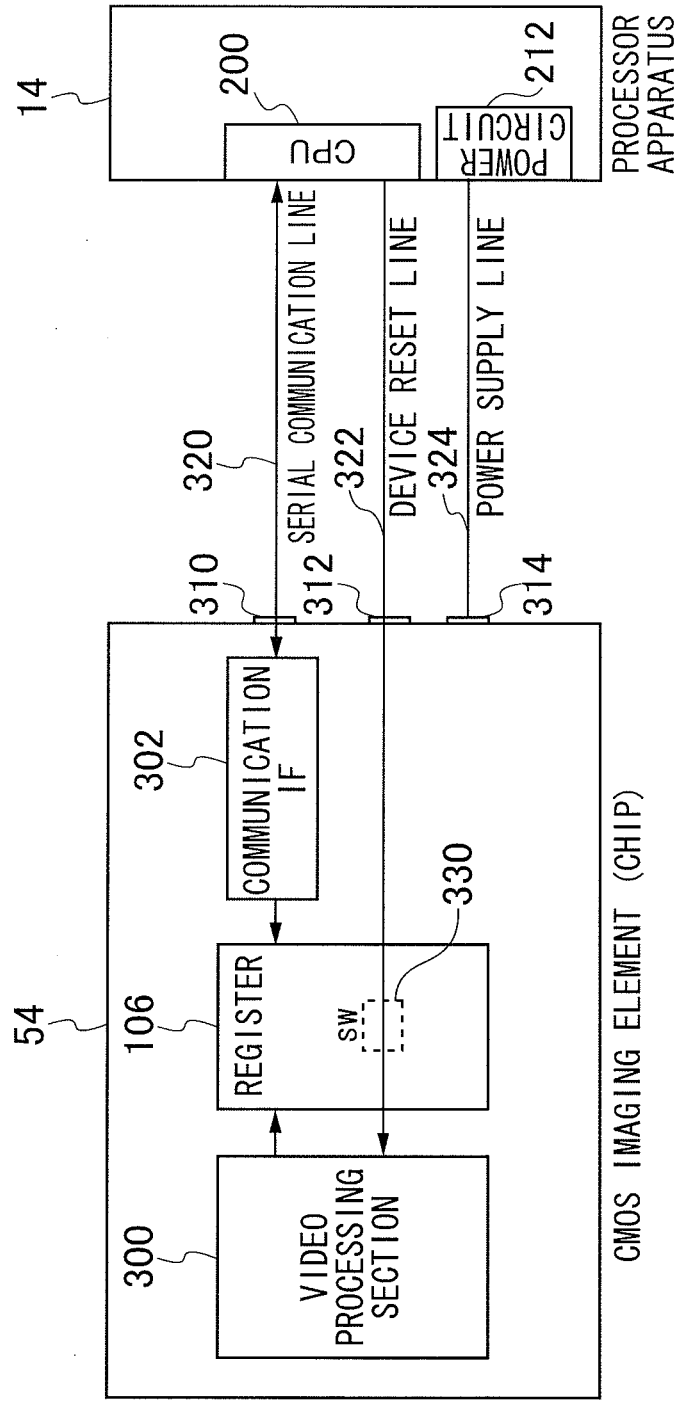
FIG. 5 is a block diagram illustrating a configuration section relating to reset of a CMOS imaging element.

FIG. 5 is a block diagram illustrating a connection line between a configuration section relating to reset of the CMOS imaging element 54 and the processor apparatus 14. In FIG. 5, a video processing section (a signal processing section) 300 representing the configuration section relating to the signal processing such as the AFE 100 and the format conversion circuit 102 in FIG. 4, the register 106 in FIG. 4, and a communication interface (a communication IF) 302 of the interface circuit 108 in FIG. 4 which performs serial communication with the CPU 200 are shown in the CMOS imaging element 54. A serial communication terminal 310, a device reset terminal 312, and a power terminal 314 are also provided as a chip terminal on the CMOS imaging element 54. A serial communication line 320 which connects the CPU 200 of the processor apparatus 14 and the serial communication terminal 310, a device reset line 322 which connects the CPU 200 and the device reset terminal 312, and a power supply line 324 which connects the power circuit 212 of the processor apparatus 14 and the power terminal 314 are also shown.

The register 106 is the memory which stores the value that determines the control content of the CMOS sensor 58 or the processing content of the video processing section 300 (VH width, shutter speed or the like) as described above. Each section of the CMOS imaging element 54 executes the processing according to the value in the register 106 by reference to the value in the register 106.

The communication IF 302 is connected to the serial communication terminal 310 inside the CMOS imaging element 54. When receiving a control signal (a command) from the CPU 200 of the processor apparatus 14 through the serial communication line as described above, the communication IF 302 decodes the control signal and sets a set value according to the content of the control signal in the register 106. The processing instructed by the control signal is thereby executed in each section such as the video processing section 300.

Figure 6:
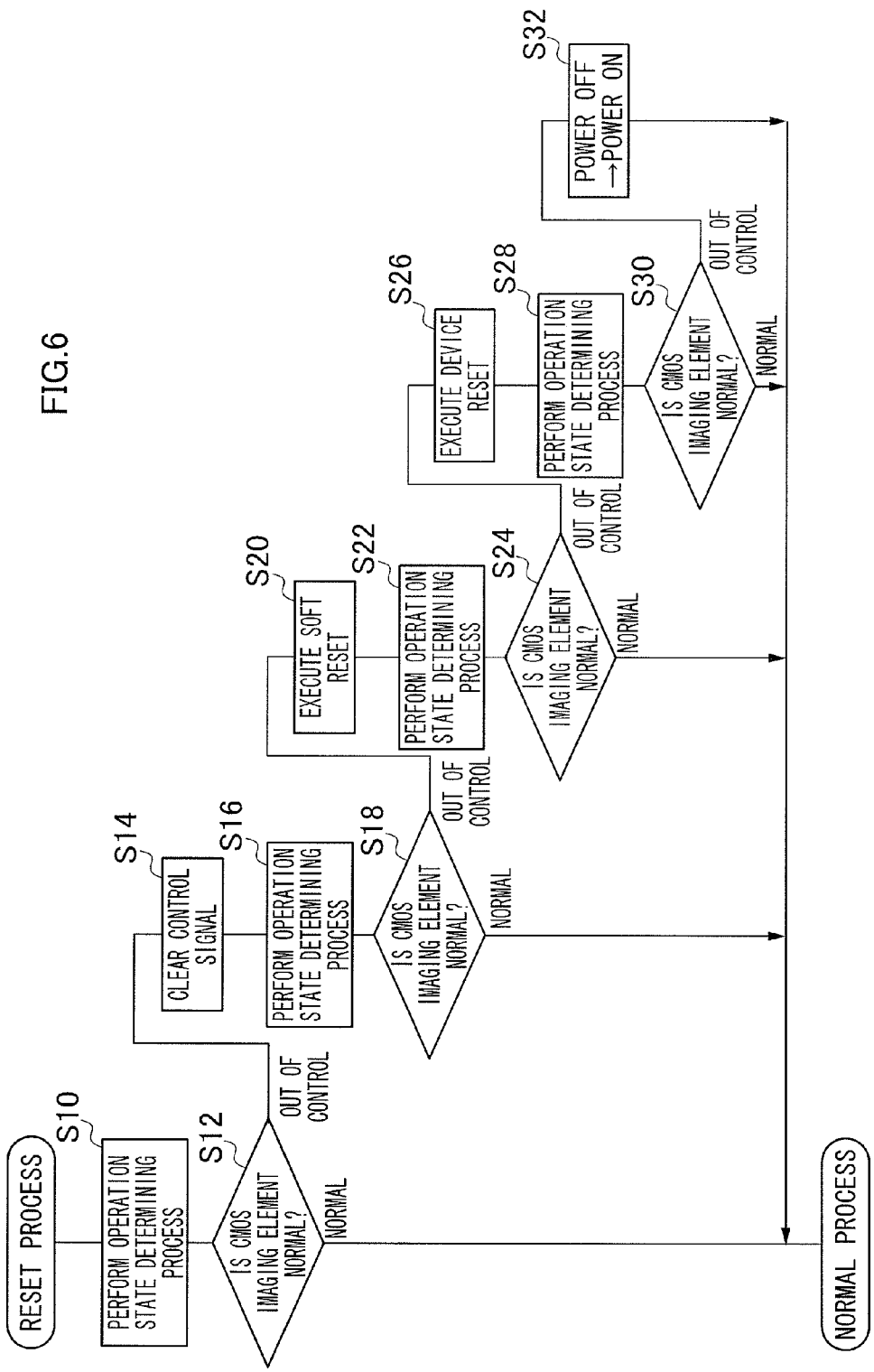
FIG. 6 is a flowchart illustrating the procedure of a method for resetting a CMOS imaging element.

FIG. 6 is a flowchart illustrating the procedure of the resetting method when the CMOS imaging element 54 having the configuration as shown in FIG. 5 is out of control.

For example, when the CPU 200 of the processor apparatus 14 transmits a control signal to give a predetermined control instruction to the CMOS imaging element 54 through the serial communication line 320 as normal processing while the CMOS imaging element 54 is taking an image, the CPU 200 waits until a response signal indicating that the control signal has been received is transmitted from the CMOS imaging element 54. In a case where the response signal is not transmitted after passage of a predetermined time period, the CPU 200 transmits the same control signal again and waits until the response signal is transmitted. The CPU 200 repeats the processing up to a predetermined number of times until the response signal is transmitted (step S10). The processing is referred to as an operation state determining process of the CMOS imaging element 54.

The CPU 200 determines whether the CMOS imaging element 54 is in a normal state or in an abnormal state (out of control) based on whether or not the response signal is finally obtained from the CMOS imaging element 54 after performing the operation state determining process of the CMOS imaging element 54 (step S12). When it is determined that the CMOS imaging element 54 is in a normal state, the operation proceeds to normal processing (a normal process).

Meanwhile, when it is determined that the CMOS imaging element 54 is out of control, the CPU 200 transmits a control signal to eliminate the control signals accumulated in the communication IF 302 since there is a possibility that an incorrect control signal has been given to the communication IF 302 due to noise on the serial communication line (step S14).

The CPU 200 then executes the operation state determining process in a similar manner to steps S10 and S12 (step S16) to determine whether or not the CMOS imaging element 54 is in a normal state (step S18).

When it is determined that the CMOS imaging element 54 is in a normal state in step S18, the operation proceeds to the normal process. When it is determined that the CMOS imaging element 54 is out of control, the CPU 200 recognizes that there is a problem with the CMOS imaging element 54, and sequentially performs the following processes to reset the CMOS imaging element 54.

First, the CPU 200 executes soft reset where the CMOS imaging element 54 can be restored to a normal operation at high speed (step S20). The soft reset is executed by transmitting a control signal to execute the soft reset through the serial communication line 320 from the CPU 200. When the communication IF 302 receives the control signal, the data recorded in the register 106 is all initialized. The CPU 200 executes the operation state determining process in a similar manner to steps S10 and S12 (step S22) to determine whether or not the CMOS imaging element 54 is in a normal state (step S24). When it is determined that the CMOS imaging element 54 is in a normal state, the reset process is terminated, and the operation proceeds to the normal process.

When it is determined that the CMOS imaging element 54 is out of control in step S24, the CPU 200 subsequently executes device reset (step S26). The device reset is performed by transmitting a predetermined reset signal (a pulse signal) to the device reset terminal 312 provided as the chip terminal on the CMOS imaging element 54 as shown in FIG. 5. The video processing section 300 is initialized by the device reset. The CPU 200 executes the operation state determining process in a similar manner to steps S10 and S12 (step S28) to determine whether or not the CMOS imaging element 54 is in a normal state (step S30). When it is determined that the CMOS imaging element 54 is in a normal state, the reset process is terminated, and the operation proceeds to the normal process.

When it is determined that the CMOS imaging element 54 is out of control again in step S30, the CPU 200 recognizes that there is a problem with the entire CMOS imaging element 54, and temporarily stops (OFF) power supply to the power terminal 314 of the CMOS imaging element 54 from the power circuit 212 through the power supply line 324, and restarts (ON) the power supply after passage of a predetermined time period (step S32).

When the power supply is temporarily stopped and restarted, the CMOS imaging element 54 is reliably restored to a normal state unless the CMOS imaging element 54 is broken. Thus, the operation proceeds to the normal process.

It is necessary to set the set value in the register 106 again after performing the reset process of any of the soft reset (step S20), the device reset (step S26), and the power supply stop and restart (step S32). The register 106 may be set again after the CMOS imaging element 54 is determined to be in a normal state by each of the reset process and the operation proceeds to the normal process. Alternatively, the register 106 may be set again along with the operation state determining process by the control signal transmitted from the CPU 200 to the CMOS imaging element 54 when the operation state determining process is executed after the soft reset and the device reset.

The aforementioned method of the operation state determining process is just an example, and the CMOS imaging element 54 may be determined whether to be in a normal state or not by another method. For example, the imaging signal output from the CMOS imaging element 54 is a digital signal, and can contain desired additional information. Thus, the imaging signal may be allowed to contain information indicating the operation state of the CMOS imaging element 54 as the additional information, the processor apparatus 14 may extract the additional information from the imaging signal obtained from the CMOS imaging element 54, and the CPU 200 may thereby determine whether or not the operation state of the CMOS imaging element 54 is normal based on the additional information. Alternatively, the CPU 200 may monitor a change in the endoscope image (a moving image) generated by the imaging signal obtained from the CMOS imaging element 54, to determine whether or not the CMOS imaging element 54 is normal based on the change. For example, when there is no change in the endoscope image, the CMOS imaging element 54 can be determined to be not in a normal state.

Also, in the aforementioned embodiment, there is a possibility that noise occurs on the device reset line 322 connected to the device reset terminal 312 of the CMOS imaging element 54, and the device reset is unintentionally executed. Thus, the device reset may be selectively enabled and disabled based on the set value of a predetermined address in the register 106 (a switch 330 of the register in FIG. 5 corresponds thereto), so that the device reset may be enabled in an initial state after the power is turned ON, and may be switched to a disabled state by rewriting the set value in the register 106 by a control signal transmitted from the CPU 200 to the communication IF 302.

The CPU 200 of the processor apparatus 14 may not be directly connected to the interface circuit 108 (the communication IF 302) of the CMOS imaging element 54, but the control circuit in the endoscope 12 such as the CPU 112 of the relay board 110 in the endoscope 12 may be connected thereto as described above. Accordingly, the exchange of signals between the CPU 200 of the processor apparatus 14 and the CMOS imaging element 54 may be performed via the control circuit in the endoscope 12, or the control circuit in the endoscope 12 may control the CMOS imaging element 54. In this case, the above reset control may be partly or entirely performed by the control circuit in the endoscope 12, not the CPU 200. Also, there is a case in which the start and stop of power supply to the CMOS imaging element 54 is controlled by the control circuit in the endoscope 12 in any of the cases in which the CPU 200 of the processor apparatus 14 is directly connected to the interface circuit 108 of the CMOS imaging element 54 and the control circuit in the endoscope is connected to the interface circuit 108 of the CMOS imaging element 54. In this case, the control circuit in the endoscope 12 performs the control on the start and stop of power supply to the CMOS imaging element 54 in the procedure of the resetting method. Moreover, the CPU 112, the relay board 110 and the control circuit described above may be provided at the position of the connector 36 or the like of the universal cord 24 of the endoscope 12, and the present invention is not limited to the case where the CPU 112, the relay board 110 and the control circuit are provided at the operation portion 22.

What is claimed is:

1. A method for resetting a CMOS imaging element in an endoscope apparatus where a CMOS imaging element which takes an endoscope image is provided at a distal end of an insertion portion, the method restoring the CMOS imaging element to a normal state when the CMOS imaging element is out of control, comprising:

a first reset step of executing soft reset to initialize a register of the CMOS imaging element;

a second reset step of executing device reset to initialize a signal processing section of the CMOS imaging element when the CMOS imaging element is not restored to a normal state by the first reset step; and a third reset step of temporarily stopping power supply to the CMOS imaging element and restarting the power supply when the CMOS imaging element is not restored to a normal state by the second reset step, wherein the endoscope apparatus is connected to a processor apparatus which processes an imaging signal output from the CMOS imaging element and displays an endoscope image on a monitor.

2. The method for resetting a CMOS imaging element in an endoscope apparatus according to claim 1, wherein
the endoscope apparatus is connected to a processor apparatus which processes an imaging signal output from the CMOS imaging element and displays an endoscope image on a monitor, and
the first reset step is executed by a control signal given from the processor apparatus or a control circuit in the endoscope apparatus to a serial communication terminal of the CMOS imaging element.

3. The method for resetting a CMOS imaging element in an endoscope apparatus according to claim 1, wherein
the endoscope apparatus is connected to a processor apparatus which processes an imaging signal output from the CMOS imaging element and displays an endoscope image on a monitor, and
the second reset step is executed by a reset signal given from the processor apparatus or a control circuit in the endoscope apparatus to a device reset terminal of the CMOS imaging element.

4. The method for resetting a CMOS imaging element in an endoscope apparatus according to claim 2, wherein
the endoscope apparatus is connected to a processor apparatus which processes an imaging signal output from the CMOS imaging element and displays an endoscope image on a monitor, and
the second reset step is executed by a reset signal given from the processor apparatus or a control circuit in the endoscope apparatus to a device reset terminal of the CMOS imaging element.

5. The method for resetting a CMOS imaging element in an endoscope apparatus according to claim 1, wherein
the endoscope apparatus is connected to a processor apparatus which processes an imaging signal output from the CMOS imaging element and displays an endoscope image on a monitor, and
the third reset step is executed by temporarily stopping power supply from the processor apparatus or a control circuit in the endoscope apparatus to a power terminal of the CMOS imaging element.

6. The method for resetting a CMOS imaging element in an endoscope apparatus according to claim 4, wherein
the endoscope apparatus is connected to a processor apparatus which processes an imaging signal output from the CMOS imaging element and displays an endoscope image on a monitor, and
the third reset step is executed by temporarily stopping power supply from the processor apparatus or a control circuit in the endoscope apparatus to a power terminal of the CMOS imaging element.

7. The method for resetting a CMOS imaging element in an endoscope apparatus according to claim 1, wherein
the endoscope apparatus is connected to a processor apparatus which processes an imaging signal output from the CMOS imaging element and displays an endoscope image on a monitor, and
whether or not the CMOS imaging element is in a normal state is determined based on whether or not there is a response from the CMOS imaging element to a control signal transmitted from the processor apparatus or a control circuit in the endoscope apparatus to a serial communication terminal of the CMOS imaging element.

8. The method for resetting a CMOS imaging element in an endoscope apparatus according to claim 6, wherein
the endoscope apparatus is connected to a processor apparatus which processes an imaging signal output from the CMOS imaging element and displays an endoscope image on a monitor, and
whether or not the CMOS imaging element is in a normal state is determined based on whether or not there is a response from the CMOS imaging element to a control signal transmitted from the processor apparatus or a control circuit in the endoscope apparatus to a serial communication terminal of the CMOS imaging element.

9. The method for resetting a CMOS imaging element in an endoscope apparatus according to claim 1, wherein
the endoscope apparatus is connected to a processor apparatus which processes an imaging signal output from the CMOS imaging element and displays an endoscope image on a monitor, and
whether or not the CMOS imaging element is in a normal state is determined by including additional information indicating an operation state of the CMOS imaging element in the imaging signal in the CMOS imaging element and reading out the additional information by the processor apparatus.

10. The method for resetting a CMOS imaging element in an endoscope apparatus according to claim 6, wherein
the endoscope apparatus is connected to a processor apparatus which processes an imaging signal output from the CMOS imaging element and displays an endoscope image on a monitor, and
whether or not the CMOS imaging element is in a normal state is determined by including additional information indicating an operation state of the CMOS imaging element in the imaging signal in the CMOS imaging element and reading out the additional information by the processor apparatus.

11. The method for resetting a CMOS imaging element in an endoscope apparatus according to claim 1, wherein
the endoscope apparatus is connected to a processor apparatus which processes an imaging signal output from the CMOS imaging element and displays an endoscope image on a monitor, and
whether or not the CMOS imaging element is in a normal state is determined in the processor apparatus, based on a change in the endoscope image by the imaging signal.

12. The method for resetting a CMOS imaging element in an endoscope apparatus according to claim 6, wherein
the endoscope apparatus is connected to a processor apparatus which processes an imaging signal output from the CMOS imaging element and displays an endoscope image on a monitor, and
whether or not the CMOS imaging element is in a normal state is determined in the processor apparatus, based on a change in the endoscope image by the imaging signal.

13. The method for resetting a CMOS imaging element in an endoscope apparatus according claim 1, wherein the device reset in the second reset step can be disabled.

14. The method for resetting a CMOS imaging element in an endoscope apparatus according claim 8, wherein the device reset in the second reset step can be disabled.

15. The method for resetting a CMOS imaging element in an endoscope apparatus according claim 10, wherein the device reset in the second reset step can be disabled.

16. The method for resetting a CMOS imaging element in an endoscope apparatus according claim 12, wherein the device reset in the second reset step can be disabled.

17. The method of claim 1, wherein the first reset, second reset and third reset steps follow each other in sequential order, said second reset step is not performed when the first reset step restores the normal operation, and the third reset step is not performed when the second reset step restores the normal operation.

18. The method of claim 17, wherein prior to performing the first reset step, said method comprises determining an operation state to determine whether the imaging element is operating in a normal state, and performing the first reset step if the imaging element is not operating in the normal state in the determining step.

19. The method of claim 18, wherein after determining that the imaging element is not operating in the normal state, said method further clears control signals for the imaging element and further re-determines the operation state prior to performing the first reset step, and after determining that the imaging element is operating in the normal state as a result of: at least one of the determining operation state and the re-determining operation state, said method continues operating the imaging element in the normal state.

\* \* \* \* \*